United States Patent
Lama

(10) Patent No.: US 9,033,087 B2
(45) Date of Patent: May 19, 2015

(54) MAGNETIC COUPLING MOBILE ROBOT

(71) Applicant: Tecnomac S.r.l., Flero, Brescia (IT)

(72) Inventor: Arturo Lama, Brescia (IT)

(73) Assignee: Tecnomac S.R.L., Flero, Brescia (IT)

( * ) Notice: Subject to any disclaimer, the term of this patent is extended or adjusted under 35 U.S.C. 154(b) by 0 days.

(21) Appl. No.: 14/014,745

(22) Filed: Aug. 30, 2013

(65) Prior Publication Data

US 2013/0340529 A1    Dec. 26, 2013

Related U.S. Application Data

(63) Continuation-in-part of application No. 12/681,405, filed as application No. PCT/IB2008/053960 on Sep. 29, 2008, now Pat. No. 8,522,905.

(30) Foreign Application Priority Data

Oct. 11, 2007 (IT) .............................. BS2007A0154

(51) Int. Cl.
*B62D 1/24* (2006.01)
*G01N 29/22* (2006.01)
*F16M 13/02* (2006.01)

(52) U.S. Cl.
CPC ........... *G01N 29/226* (2013.01); *F16M 13/022* (2013.01); *Y10S 901/01* (2013.01); *G01N 29/225* (2013.01)

(58) Field of Classification Search
CPC .. A63H 18/10; A63H 18/16; A63H 2018/165
USPC ......................................... 180/167, 168, 169
See application file for complete search history.

(56) References Cited

U.S. PATENT DOCUMENTS

| | | | | |
|---|---|---|---|---|
| 2,690,626 A | * | 10/1954 | Gay et al. | 446/130 |
| 3,690,393 A | * | 9/1972 | Guy | 180/65.6 |
| 3,922,991 A | * | 12/1975 | Woods | 114/222 |
| 5,347,456 A | * | 9/1994 | Zhang et al. | 701/23 |
| 5,536,199 A | * | 7/1996 | Urakami | 451/91 |
| 2009/0078484 A1 | * | 3/2009 | Kocijan | 180/167 |
| 2010/0212983 A1 | * | 8/2010 | Lama | 180/167 |

FOREIGN PATENT DOCUMENTS

| | | | |
|---|---|---|---|
| DE | 20210484 | 9/2002 | |
| FR | 2145115 | 2/1973 | |
| FR | 2689479 | 10/1993 | |
| JP | 61200070 | 9/1986 | |
| JP | 62034865 | 2/1987 | |
| JP | 62152983 | 7/1987 | |
| JP | 62152983 A | * 7/1987 | ............ B62D 57/02 |
| JP | 09286360 | 11/1997 | |
| JP | 2001151170 | 6/2001 | |

\* cited by examiner

*Primary Examiner* — J. Allen Shriver, II
*Assistant Examiner* — Bridget Avery
(74) *Attorney, Agent, or Firm* — Davis & Bujold, P.L.L.C.; Michael J. Bujold

(57) ABSTRACT

A probe-holder carriage includes a frame which can slide over a highly magnetically permeable support surface and at least one permanent magnet able to interact magnetically with, and couple the robot to, the surface. The permanent magnet is positioned so that one pole grazes the surface and faces the surface at a minimum distance from it. The frame defines a central housing which can support at least one probe.

10 Claims, 17 Drawing Sheets

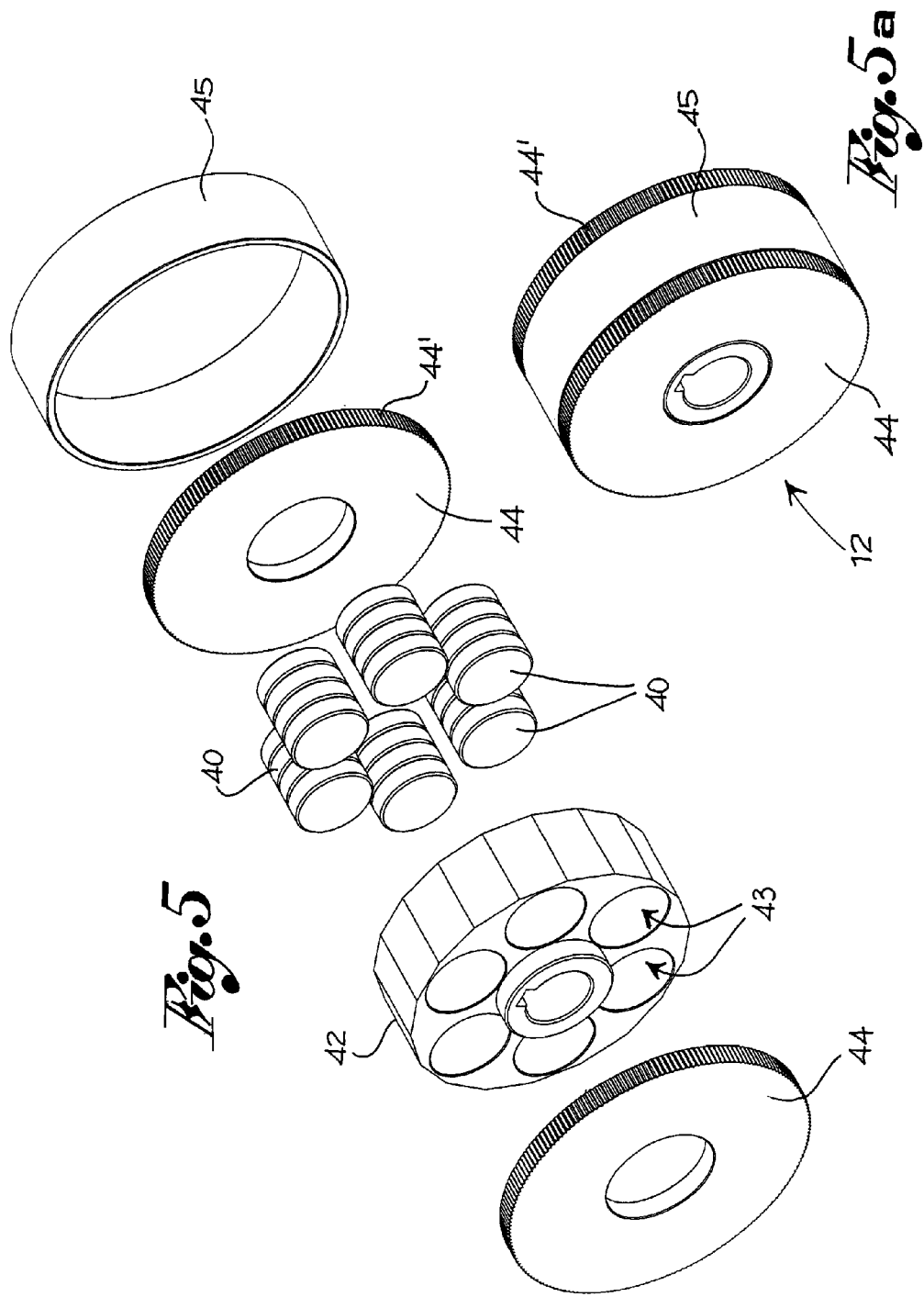

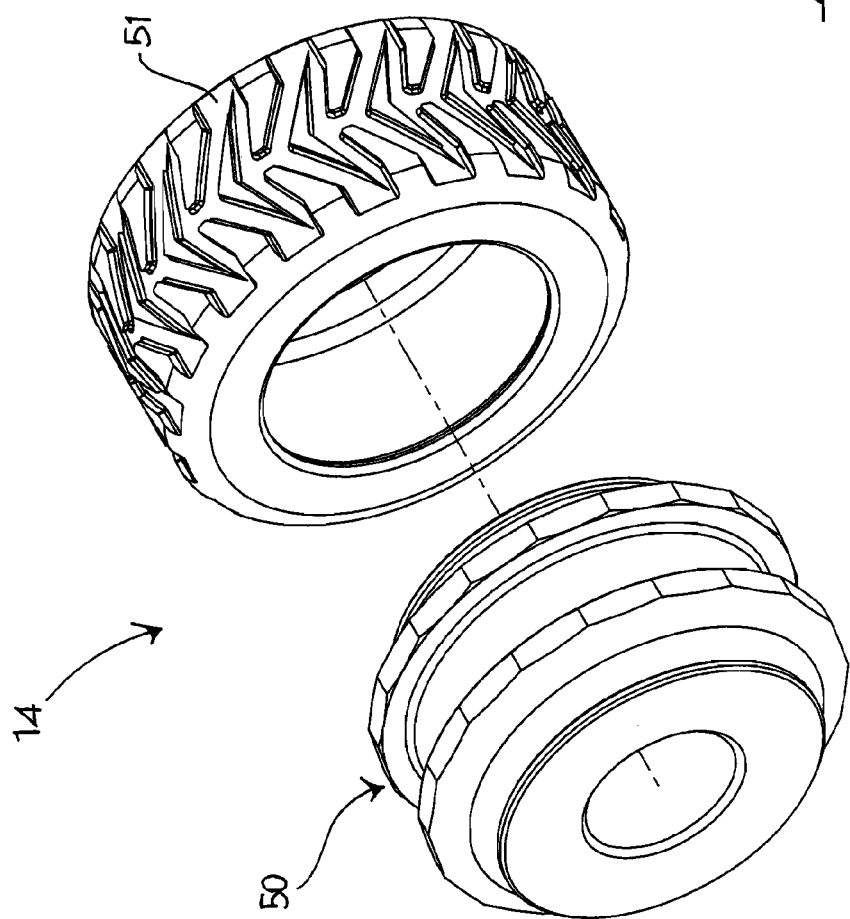

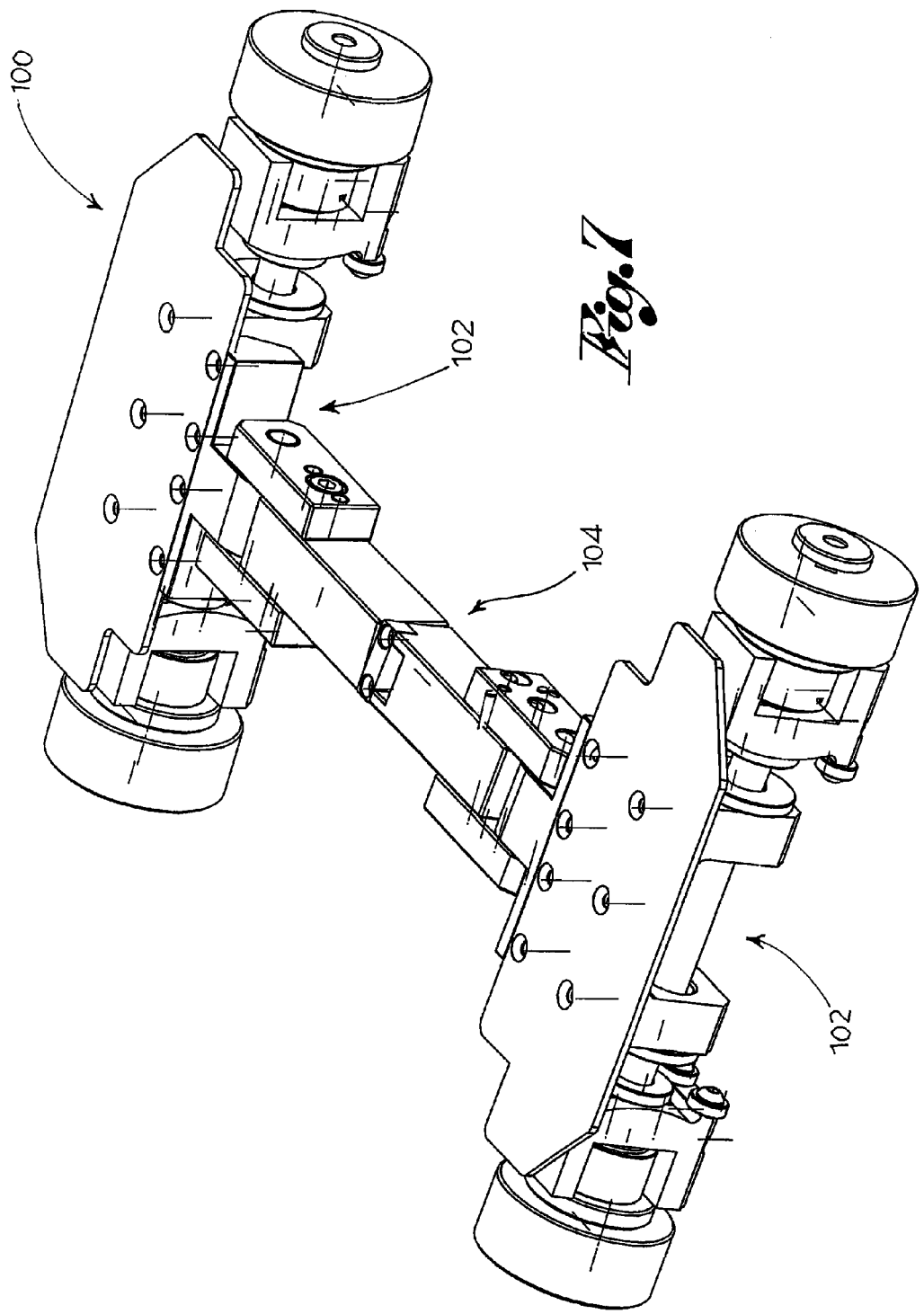

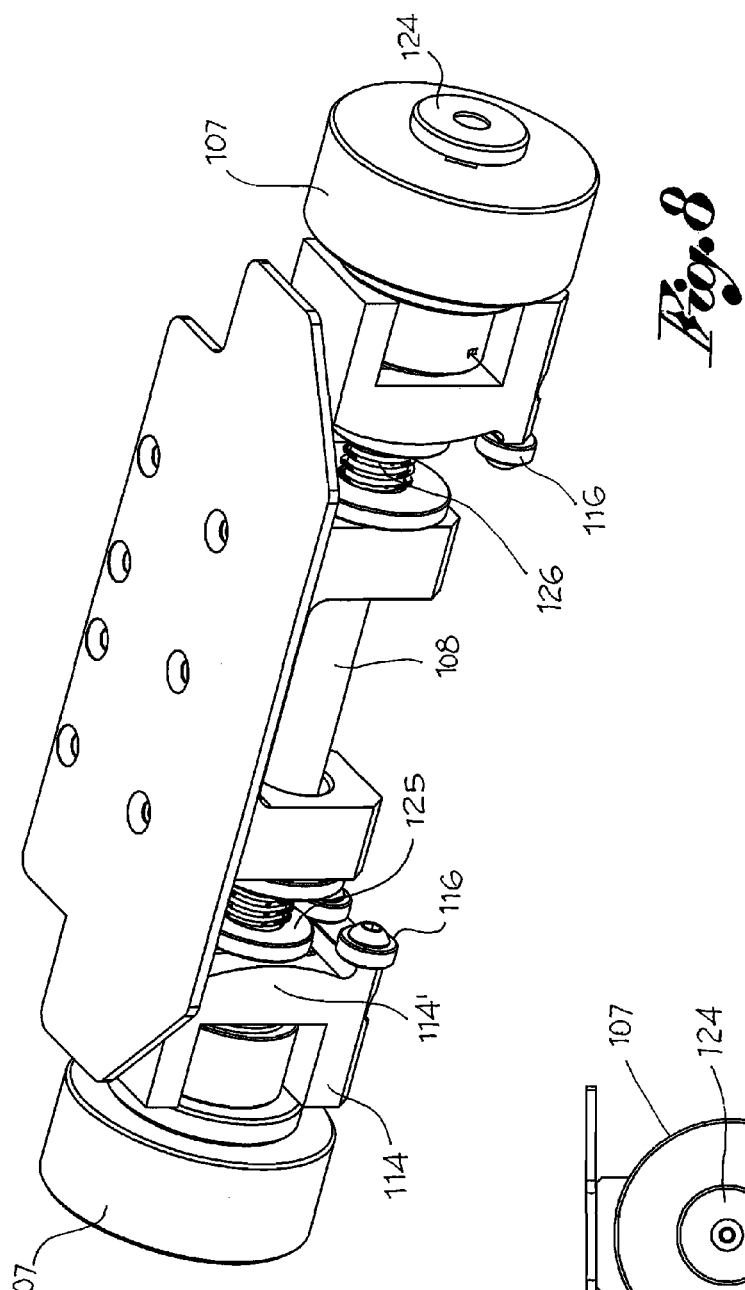
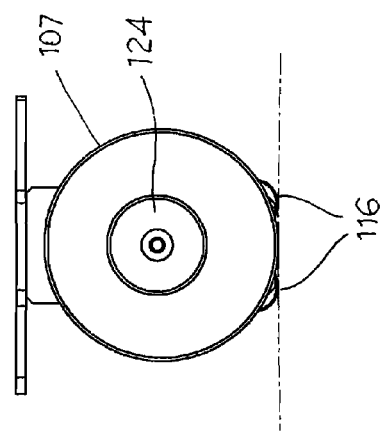

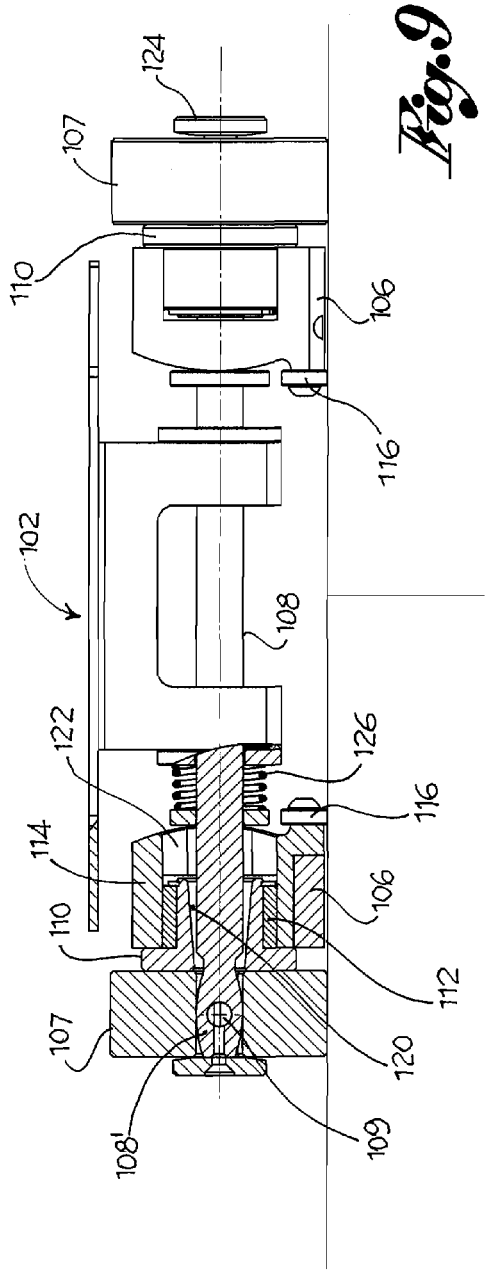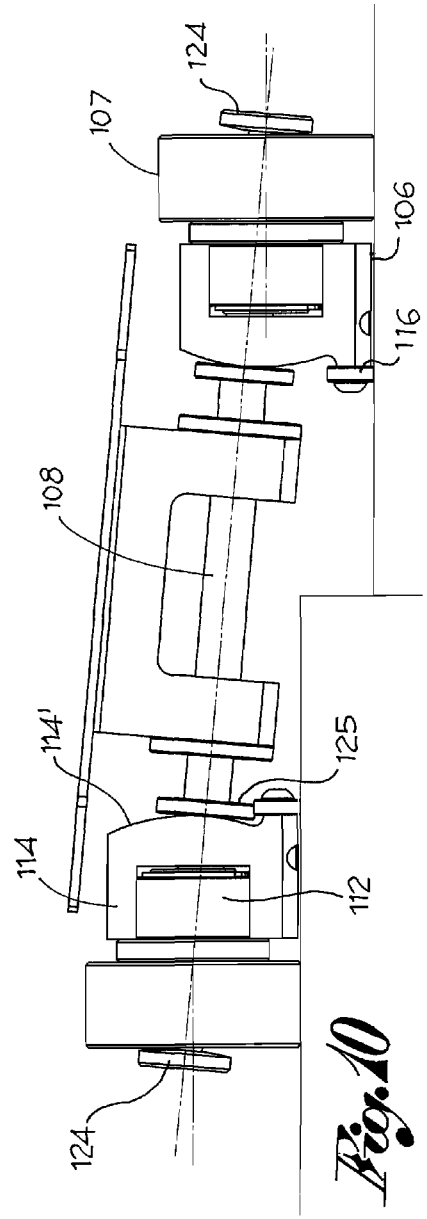

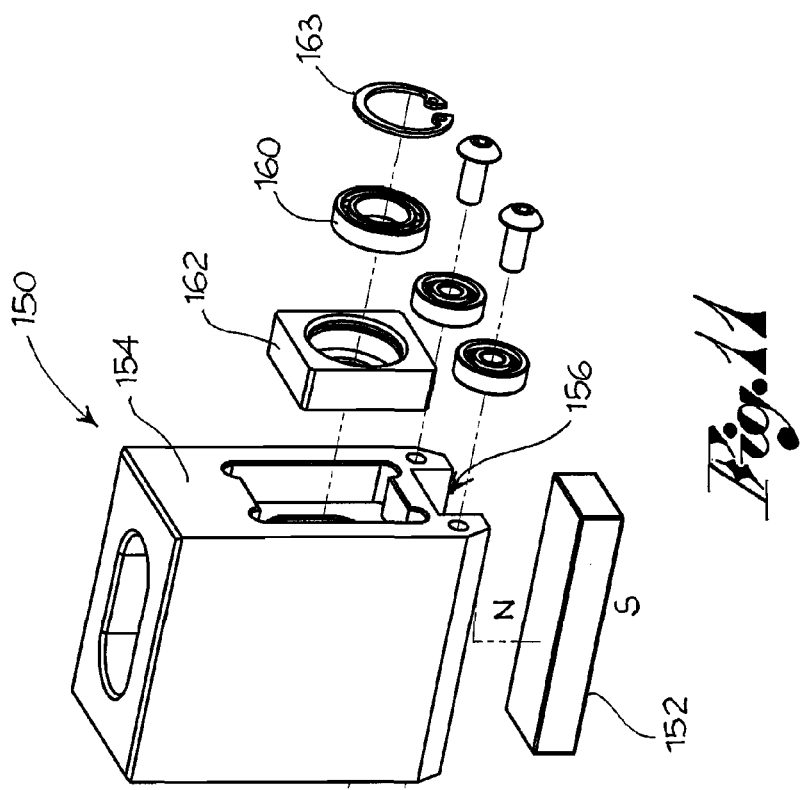
Fig. 11
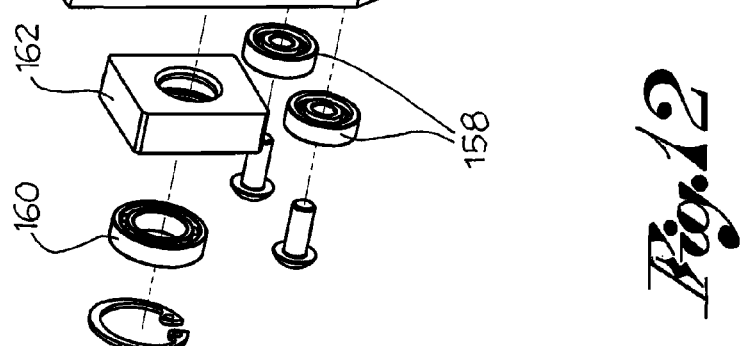
Fig. 12
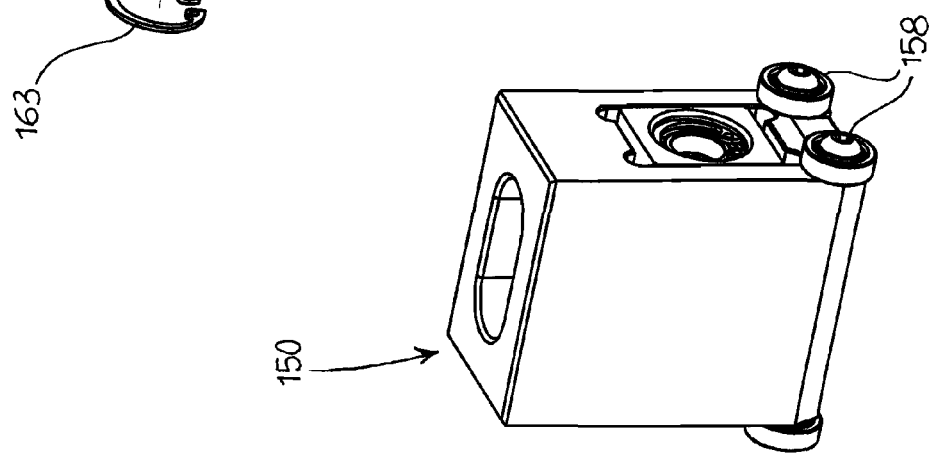

US 9,033,087 B2

MAGNETIC COUPLING MOBILE ROBOT

This application is a continuation-in-part of application Ser. No. 12/681,405, filed Apr. 2, 2010, which was the U.S. national phase of international application PCT/IB2008/053960, filed Sep. 29, 2008, which claimed convention priority from Italian patent application BS2007A000154, filed Oct. 11, 2007.

FIELD OF THE INVENTION

The present invention relates to a mobile robot with magnetic coupling.

In some applications in the art, surfaces to be processed or treated in various ways, for example, to be welded together, may be inspected by a robot provided with wheels allowing the robot to move along the surface. The robot is fitted with probes able to inspect the surface by detecting, for example, the quality of the process carried out.

When the material of which the surface is made allows it, i.e. when it is ferromagnetic, the robot is coupled magnetically to the surface by means of permanent magnets. Thanks to this anchoring system, the robot can also climb vertically or even rotate through 360°. Therefore not only flat surfaces can be inspected, but also curved—for example cylindrical—surfaces.

BACKGROUND ART

Thus far, robots with magnetic coupling have been fitted with wheels which are made, at least externally, in contact with the surface, of permanent magnets or electromagnets.

Prior art solutions exhibit one notable disadvantage. Whilst being able to function, they require enormous power to drive the wheels in order to overcome the magnetic field which tends to immobilize the wheels. It is therefore difficult to achieve free-sliding movement along the surface being inspected.

Moving the robot requires a powerful electric motor and therefore the need of electrical wiring to a remote power source, making the robot heavy and cumbersome.

SUMMARY OF THE INVENTION

The Aim of this invention is to propose a mobile robot with magnetic coupling which is able to overcome, at least partially, the disadvantages described above of the prior art robots.

This aim is achieved by a robot as described below.

BRIEF DESCRIPTION OF THE DRAWINGS

Further features and the advantages of the robot according to the present invention will appear more clearly from the following description of preferred non-limiting embodiments thereof, with reference to the attached drawings, in which:

FIG. 5 shows an exploded view of a robot wheel with auxiliary magnets;

FIG. 5*a* shows the assembled wheel;

FIG. 6 shows an exploded view of another robot wheel;

FIG. 7 shows a perspective view of the robot frame according to one different embodiment;

FIG. 8 shows an enlarged perspective view of one of the two transverse axles supporting the frame shown in FIG. 7 and enabling it to slide over a surface to be inspected;

FIG. 9 shows a partial cross-section of the transverse axle of FIG. 8;

FIG. 9*a* shows a side view of the transverse axle;

FIG. 10 shows a view of the transverse axle tilted to the horizontal;

FIG. 11 shows an exploded view of a magnet support, according to a different embodiment; and FIG. 12 shows the support of FIG. 11 duly assembled.

DETAILED DESCRIPTION OF THE INVENTION

Figure 1:
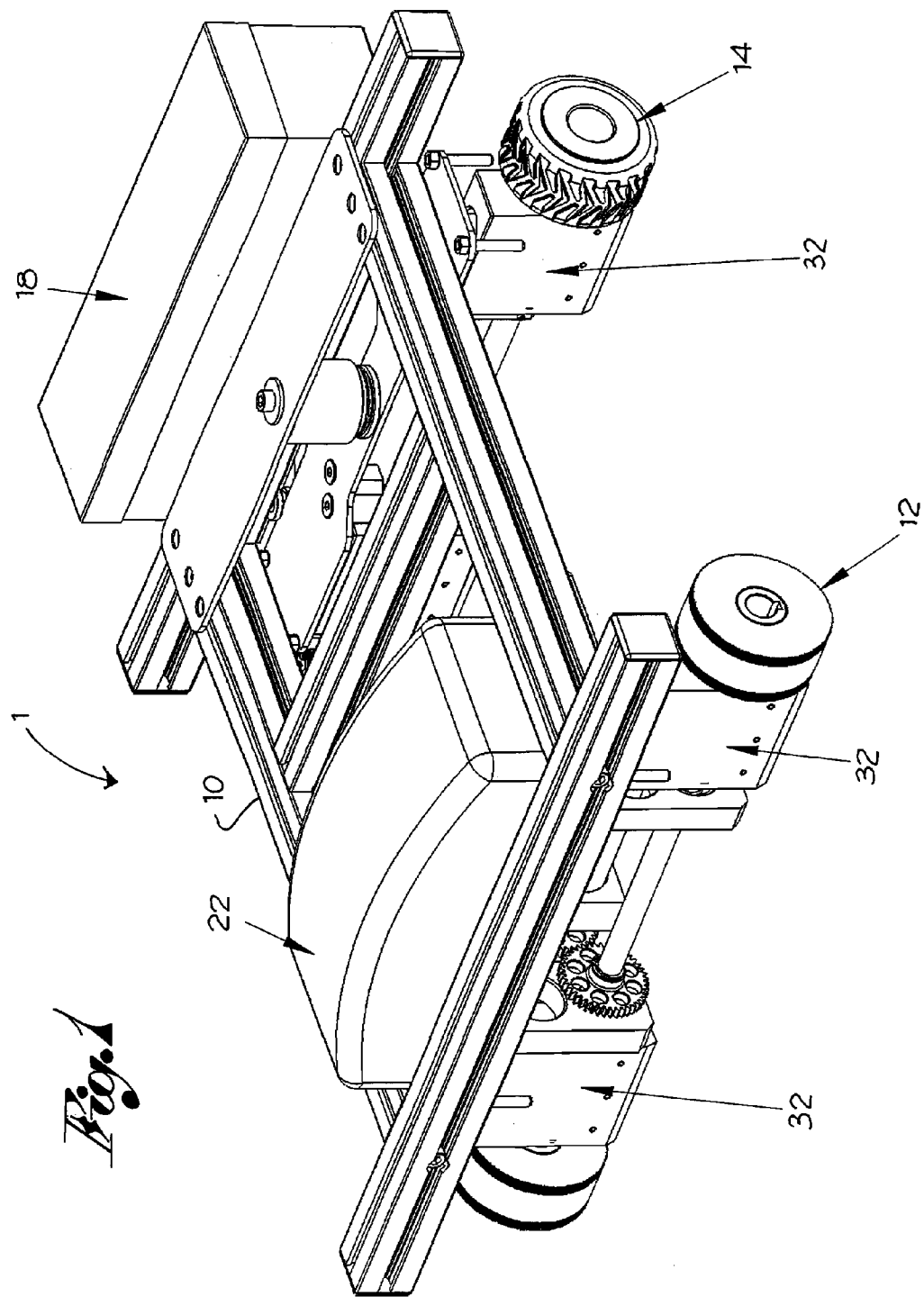
FIG. 1 shows a perspective view of a robot according to the invention.
Figure 2:
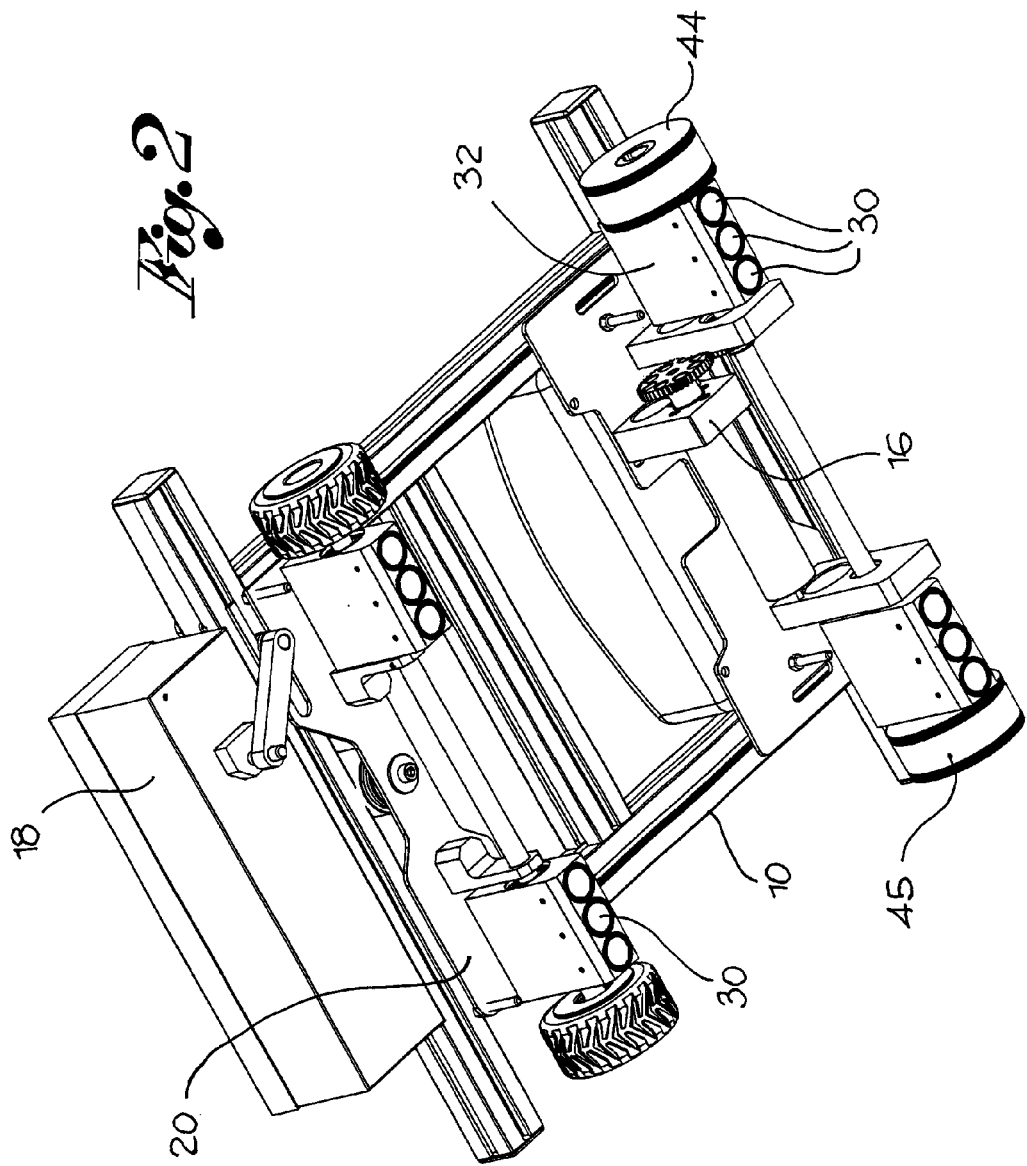
FIG. 2 shows a perspective view of the robot from below.
Figure 3:
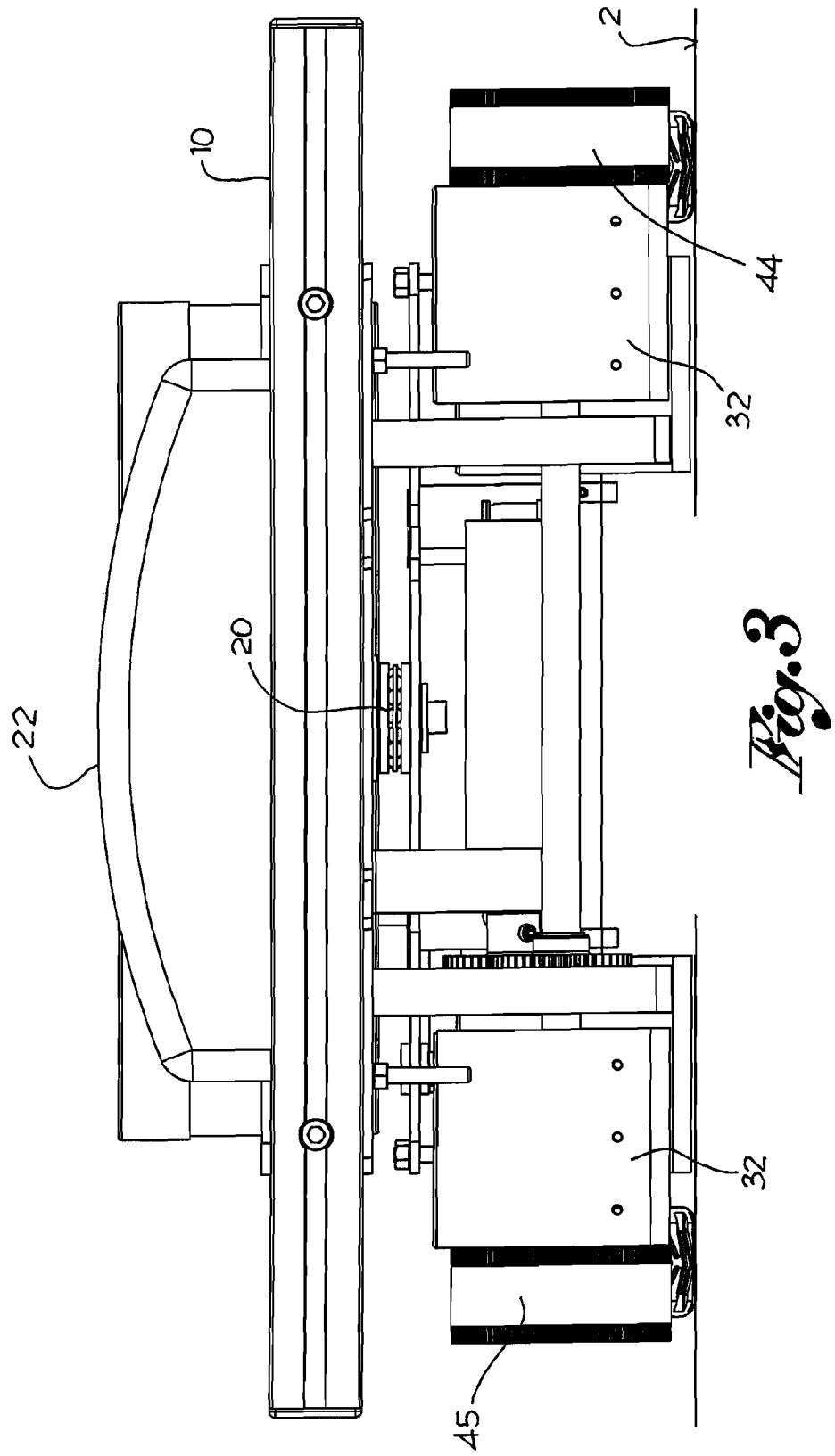
FIG. 3 shows an end view of the robot.
Figure 4:
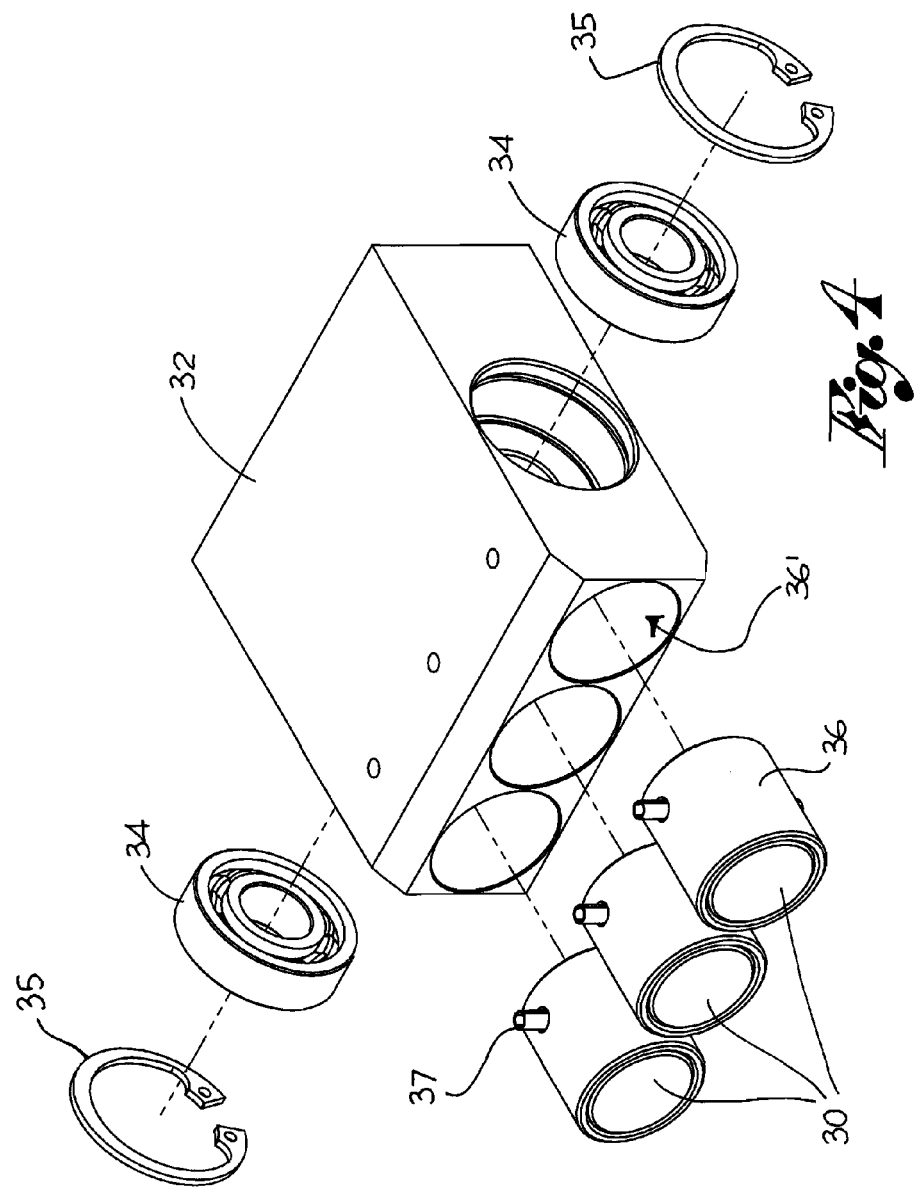
FIG. 4 shows an exploded view of a support with permanent magnets.

With reference to the above figures, numeral reference 1 globally indicates a mobile robot with magnetic coupling according to the invention.

Robot 1 includes a frame 10 with wheels 12, 14 enabling the robot to slide over a resting surface 2 which is highly magnetically permeable, for example a ferromagnetic material.

The robot 1 is in the form of a mobile carriage able to move over a surface, for example a piece of sheeting to be inspected.

In accordance with a preferred embodiment, the robot 1 is fitted with at least one driving wheel 12 enabling independent movement over the surface to which it is coupled magnetically. This does not exclude the possibility of the robot described below being moved manually along the resting surface.

In accordance with a preferred embodiment, at least one driving wheel 12 is powered by a motor reduction gear 16.

Advantageously, the motor reduction gear 16 is powered electrically with continuous voltage of, for example, 12 V, supplied by a battery 18 fitted to the frame 10 of the robot 1. Therefore, the robot does not need to be connected up to a power supply by electrical cable.

At least one wheel, for example a guided wheel 14, is connected to a steering device 20.

The robot 1 is therefore able to move forwards, backwards, to the right and left.

According to an advantageous embodiment, these movements are controlled by a remote control handset via a CPU 22 fitted to the robot frame.

In one possible embodiment, the robot is fitted with at least one permanent magnet 30 capable of magnetic interaction with the resting surface 2, so as to couple the robot to said surface.

The permanent magnet 30 is fitted so as to graze the resting surface 2. In other words, the magnet 30 is detached from the ferromagnetic surface 2, but is kept at a pre-set distance, able to generate a magnetic force of attraction such as to enable the robot 1 to remain sturdily anchored to the resting surface 2, whatever its direction or motion.

In order to maximize the density of the magnetic field acting on the resting surface 2 and therefore the force of attraction, the magnet 30 is fitted with one of its poles facing the resting surface 2. In other words, the axis of the two poles of the magnet 30 is perpendicular to the surface 2.

Clearly, the factors which determine the intensity of the magnetic field between the at least one magnet 30 and the resting surface 2, i.e. the distance between the magnet and the surface, the type, shape and size of the magnet, will be chosen on the basis of the application, the travel of the magnet, the weight of the robot (plus any load such as a probe).

In a particularly advantageous embodiment, at least one magnet 30 is fitted onto a support 32 which is allowed to oscillate freely so that the magnet is always oriented in the position of minimum distance from the resting surface, that is in the position of maximum field density.

Preferably, magnets 30 are fitted close to the points of contact between the robot 1 and the resting surface, i.e. close to the wheels 12, 14.

In the illustrated embodiment, the robot is fitted with a couple of driving wheels 12 and a couple of guided wheels 14.

In accordance with a preferred embodiment, the robot 1 is fitted with four supports 32, for example comprising essentially parallelepiped blocks, each carrying several magnets 30. Each magnet is, for example, disc or tablet shaped, and has surfaces parallel to the resting surface of the robot. The blocks 32 are advantageously fitted to the rotating shafts 13, 15 of the wheels 12, 14. Each block 32 is fitted with ball bearings 34 to enable free rotation around the shaft to which it is fitted. The ball bearings 34 are fitted to the support 32, for example by seeder 35.

In one embodiment, each magnet 30 is fixed or glued to a pillar 36, cylindrical in form for example, seated in a housing 36 inside the support 32 and held into place by a pin 37, for example.

In one embodiment, the magnets 30 are parallel to each other, for example aligned parallel to the shaft 13.

In one embodiment, the permanent magnets 30 are in neodymium.

According to an advantageous embodiment, further permanent magnets 40, henceforth called supplementary magnets, are fitted into the casing 42 of at least one couple of coaxial wheels, preferably the driving wheels 12.

In one embodiment, these supplementary magnets 40 comprise small cylinders which, when fitted into a wheel, turn the relevant axis parallel to the wheels axis. In a possible embodiment, the wheels 12 include a central cylindrical casing 42, for example in aluminum, where, around a hole for the rotating shaft 13, a crown-shaped series of cylindrical housings 43 is created which are fitted with cylindrical magnets 40.

The central casing 42 is fitted between a couple of side disks 44 made of ferromagnetic material with a milled outer surface 44 for contact with the surface 2. Advantageously, the disks 44 are fixed to the central casing 42 by means of the magnetic field generated by the supplementary magnets 40.

Around the rotating surface 42' of the central casing 42 of the wheel 12 an anti-slip fascia 45, made of rubber or similar type of material, is fitted.

The function of the supplementary magnets 40 is to generate a magnetic field interacting with the resting surface 2 of ferromagnetic material, in order to ensure that the fascia 45 always adheres to resting surface 2, preferably by exerting optimum pressure on it. In this way the wheels do not slip on the support surface, in particular the driving wheels, even when the surface 2 is damp, for example to facilitate ultrasound measurements.

Advantageously, the fascia 45 is kept in position by two side discs 44, clamping from opposite sides of the wheel.

Clearly, given its position on the wheels, the crown of supplementary magnets 40 acts on the resting surface 2 one magnet at a time, the one closest to the surface as the wheel rotates. This advantageously produces the desired effect of increasing the adherence of the robot to the surface, by preventing the slippage of the wheels, without preventing their proper rotation once they have made contact with the ferromagnetic surface.

In terms of the structure of the wheels, the central casing 42 of the driving wheels 12 and/or the casing 50 of the guide wheels 14 has a multi-faceted rolling surface, i.e. a polygonal shape able to improve the anti- slip effect still further.

On the casing 50 of the guide wheels 14, for example, a tooled tire 51 can be fitted.

In accordance with the embodiment illustrated in FIGS. 7-10 and with the invention, the robot has a frame 100 with longitudinal axle 101 connecting two transverse axles 102 for the purposes of sliding along the ferromagnetic surface to be inspected. The longitudinal axle 101 has an articulated joint 104 enabling the two transverse axles 102 to rotate independently of the longitudinal axle. This enables the robot to move along uneven or rough surfaces, for example along weld lines to be checked, without losing adherence, as shown in FIG. 10.

In accordance with a preferred embodiment, near each wheel 107 of the robot, each axle 102 is fitted with a permanent magnet 106. The wheel 107 may advantageously include supplementary magnets and/or may be fitted with a tire and/or multi-faceted rolling surface, as described above in relation to FIGS. 5 and 6.

Every wheel 107 is fitted to the end of a rotating shaft 108, for example by means of a clamping pin 109. A support flange 110 for at least a ball bearing 112 extends axially and inwardly from the wheel 107. On the bearing 112 an oscillating support 114 is fitted for at least one permanent magnet 106 coupling the robot to the resting surface.

This support 114 has a cavity underneath where the permanent magnet 106 is fitted, for example, by pressure, with one of the two opposing poles facing the ferromagnetic surface. In accordance with one embodiment, this magnet 106 is rectangular, longer and wider than thick, and with the largest surfaces parallel to the ferromagnetic surface. The face of the permanent magnet facing the sliding surface is kept at such a height that it grazes said surface without being in actual contact.

In accordance with a particularly advantageous embodiment, the support 114 for the magnet 106 is in contact with the sliding surface via a roller 116, or preferable two rollers, for example made with ball bearings. Clearly, through this double support given by wheel 107 and rollers 116, the magnet is enabled to be as close to the ferromagnetic surface as possible, without the risk of making contact.

In other words, the rollers 116 act, together with the wheel, as spacers guaranteeing a slight distance between the magnet and the ferromagnetic surface.

For the transverse axles 102 to rotate about the longitudinal axle of the frame whilst at the same guaranteeing that the wheels and rollers adhere to the sliding surface, the shaft 108 must be capable of tilting in relation to the wheels 107 and the oscillating support 114 of the magnet.

For this purpose, in accordance with a particularly advantageous embodiment, the axial housing 120 for the rotating shaft 108 which crosses the flange 110 of the bearing support has a conical shape, widening towards the inside, allowing the shaft 108 to tilt in relation to the flange axis.

In accordance with one embodiment, the support 114 of the magnet has an axial portion 114' extending towards the inside, beyond the bearing, so as to house a magnet 106 which is longer than the bearing width. A slot-shaped aperture 122 provided in said axial portion 114' receives the rotating shaft 108 allowing the shaft to oscillate in relation to the support.

In accordance with one embodiment, the end 108' of the rotating shaft to which the wheel 107 is fitted has a rounded outer surface, for example ogival, so it can oscillate inside the axial hole of the wheel 107.

Advantageously, the wheel 107, flange 110 and support 114 of the magnet are clamped together along the axis by an outer washer 124, attached to the wheel 107 and screwed tight to the end of the rotating shaft 108 and an inner washer 125, around the rotating shaft and pressed against the magnet support, for example by a spring 126.

Therefore, the wheel, flange with bearing and magnet support are pack-assembled in order to make a single wheel unit with the magnet in position hovering over the sliding surface.

FIGS. 11 and 12 show another embodiment of an oscillating support 150 for at least one magnet 152. This embodiment is particularly suitable for applications with small diameter pipes, for example diameters of less than 1 meter, where the robot must be compact. A single oscillating support 150, in this embodiment, is fitted centrally to at least one of the two rotating shafts of the wheels.

The support 150 includes a prism-shaped casing 154, with a face turned to the sliding surface in which there is a housing 156 for at least one permanent magnet 152, arranged, as described before, with one pole turned to the ferromagnetic surface to be inspected. Preferably, the magnet 152 is rectangular or bar-shaped and fitted horizontally, for example, pressed into the housing 156.

Contact between the support 150 and sliding surface is by means of lateral rollers 158, for example two for each end of the support, preferably fixed to the appendices outlining the housing 156 of the magnet. These rollers 158 act as spacers similarly to the description above for the support element 114.

To provide oscillation, the support 150 is fitted to the rotating shaft by means of a couple of bearings 160, seated in respective housings 162 clamped to the support casing, for example, by a seeder 163.

In accordance with an advantageous embodiment, the bearings 160 are of the oscillating type, in order to allow the rotating shaft, in this case too, to oscillate, albeit less than in the previous example with the dual oscillating support for each transverse axle.

The robot according to the invention is particularly suitable for carrying a probe for the purposes of carrying out the non-destructive testing of weld lines and the seal of metal plating, for example carbon steel. In particular, the robot 1 is designed for applications involving cylindrical sheeting (for example tanks of great length or large diameter) made by calendaring and welding flat sheeting. It should be noted that, for ultra-sound probes to work to best effect, these metal sheets need to be damp.

The robot is hooked up to the sheeting to be inspected via a permanent magnetic field generated by magnets at some distance from the sheeting and hence without impeding the rotation of the wheels, as occurs in prior art robots. Therefore a powerful motor is not required. A small motor reduction gear is sufficient, powered by a 12 V battery.

The disposition of the magnets 30, 40, 106, 152 allows the robot to climb vertically with its load, and to rotate through 180° without losing adherence, even on a damp and slippery surface.

Since the robot, according to this invention, does not require power cables for its movement, data from the probes can advantageously be transmitted in wireless mode. Therefore, the robot 1 is completely free-standing, compact and easy to handle.

According to this invention, largely due to the reduced weight of the motor, the robot has an overall weight (including the power battery) of less than 15 Kg, well below the regulatory maximum for weights to be lifted by operators (30 kg for men, 20 kg for women).

The proposed robot is therefore very simple and easy to use and transport.

In the embodiments shown in FIGS. 13-20, the probe-holder carriage 200 comprises a probe-holder frame 202 to which sliding means are connected for cooperation with a resting surface 2 in a material with high magnetic permeability so as to permit a sliding of the carriage on said surface 2. At least one permanent magnet 206, suitable for interacting magnetically with said resting surface 2 for an anchorage of the device to said surface 2, is fitted on the probe-holder frame 202 so as to graze the resting surface 2 with one of its poles.

Said at least one permanent magnet 206 is thus positioned and kept in place at a predefined distance from the resting surface 2.

In one embodiment illustrated in FIGS. 13-18, the sliding means comprise sliding skates 204 hinged to the probe-holder frame 202 so as to be free to oscillate, at least within a given angle, in relation to said probe-holder frame to adapt to a curvature of the resting surface 2. In other words, the sliding skates 204 are tipping skates and are able to tip so as to adapt even to flat surfaces. The permanent magnets 206 are supported by respective sliding skates 204.

Figures 16, 16A:
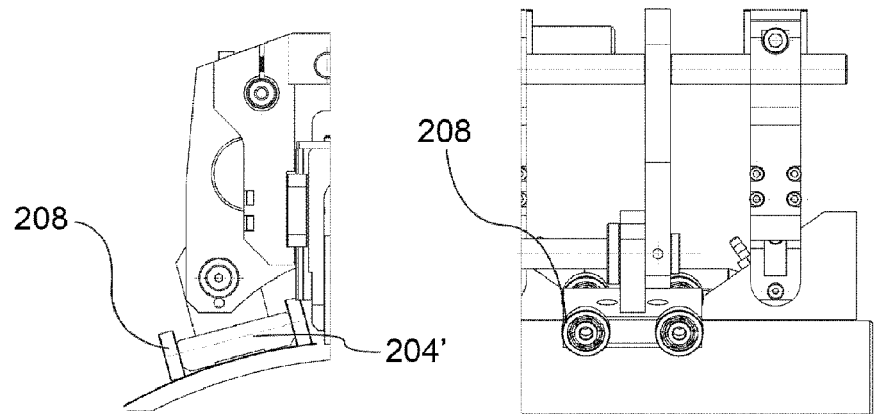
FIGS. 16 and 16*a* illustrate, in a side and end view respectively, a portion of carriage at a sliding skate in one embodiment.
Figures 17, 17A:
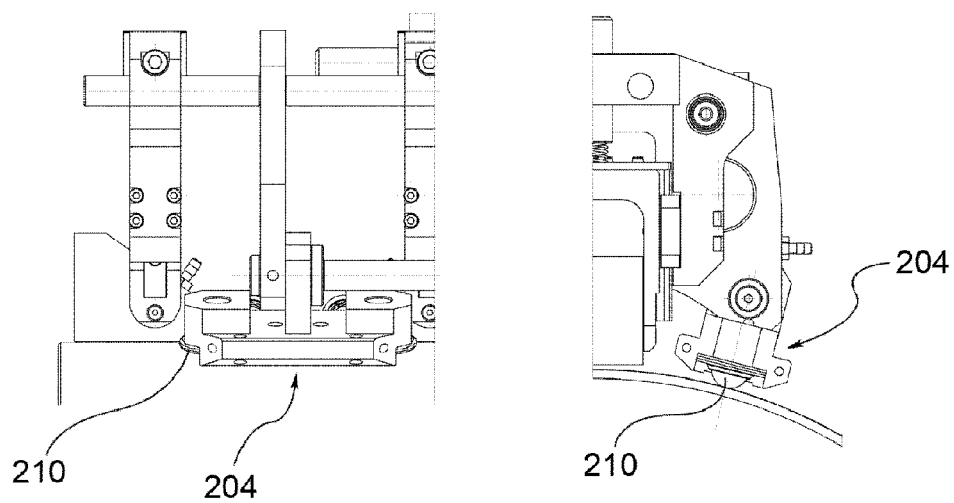
FIGS. 17 and 17*a* illustrate, in a side and end view respectively, a portion of carriage at a sliding skate in a further embodiment.
Figure 18:
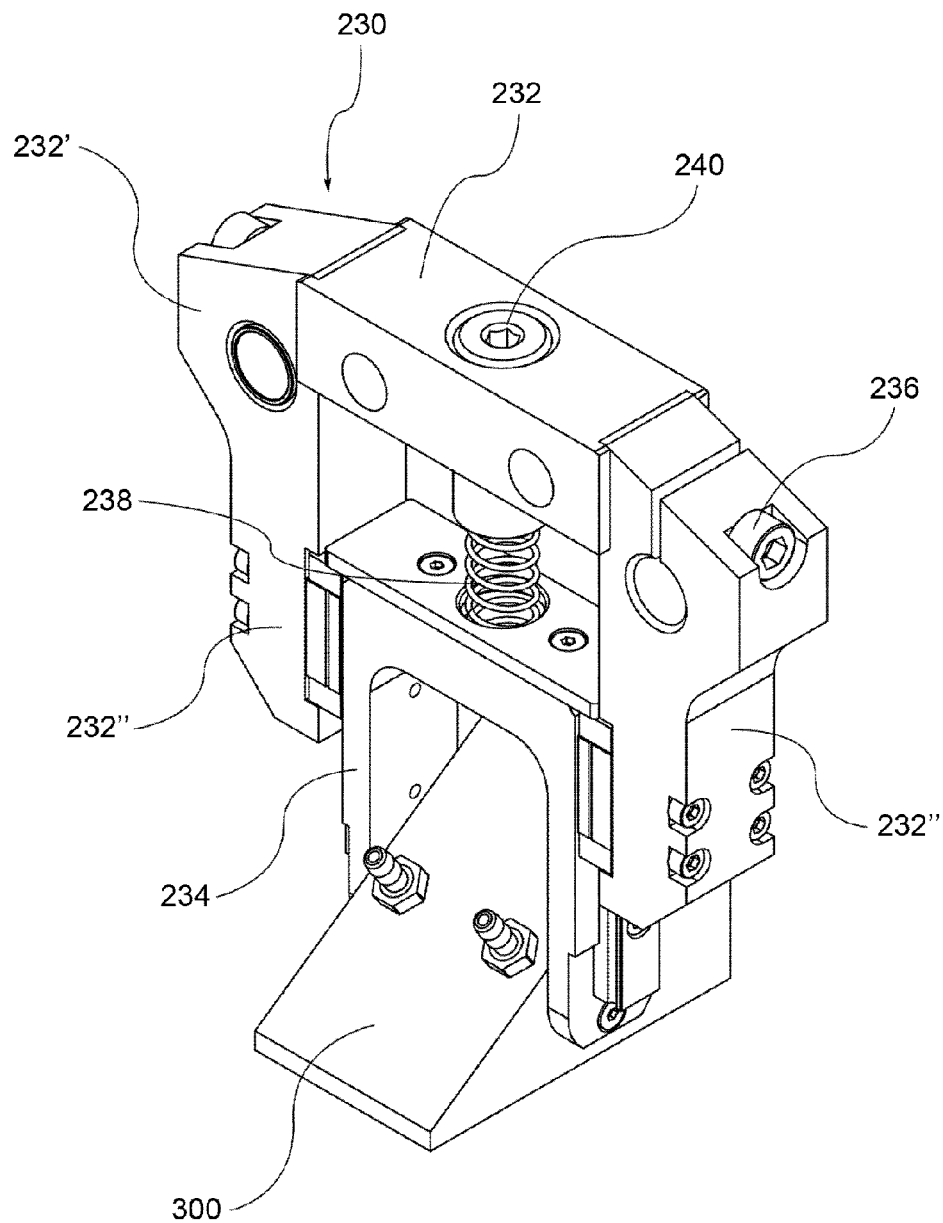
FIG. 18 shows, in perspective view, a single probe-holder bracket equipped with a probe.

In the embodiment shown in FIGS. 13-16, the sliding skates 204 are fitted with wheels 208 suitable to permit a sliding of the carriage 200 in one direction only. For example, with reference to the situation of a carriage sliding on a cylindrical surface, the carriage in FIGS. 13-15 has wheels 208 oriented with the rotation axis orthogonal to generatrices of the cylindrical surface, so as to permit a longitudinal sliding of the carriage; FIGS. 16 and 16a instead show wheels 208 oriented with the rotation axis orthogonal to generatrices of the cylindrical surface, so as to permit a circular sliding of the carriage. In another embodiment, shown in FIGS. 17 and 17a, the sliding skates are fitted with balls 210 suitable to permit a sliding of the carriage in any direction.

Each sliding skate 204 fitted with magnets comprises a block 204', for example of a parallelepiped shape, in which a seat housing the magnet 206 is made in the side facing the resting surface. The wheels 208 or balls 210 are positioned on the blocks 204' so as to ensure a stable and constant support of the skate 204 on the resting surface 2 and thus a constant and safe positioning of the magnet 206 in relation to said surface. For example, a sliding skate is fitted with four coplanar sliding wheels 208, positioned on opposite sides of the block 204', or with two balls 210 fitted centrally on the block 204'.

According to one aspect of the invention, the probe-holder frame 202 defines a central housing 202' and comprises support means suitable to support at least one probe 300 inside said central housing 202'.

In a preferred embodiment, the probe-holder frame 202 extends symmetrically in relation to a central plane P perpendicular to the resting surface 2. Advantageously, the probe or plurality of probes 300 is supported by the probe-holder frame 202 so that it too is symmetric in relation to said central pane P, so as to ensure, when it is placed in contact or next to the resting surface 2, a precise and constant positioning in relation to said surface.

In a preferred embodiment, the probe-holder frame 202 comprises two substantially vertical end plates 220. Said end plates 220 are connected by two lower lateral bars 222 and by two upper lateral bars 224. For example, said bars 222, 224 are parallel to the central plane of symmetry P mentioned above. Consequently, the two end plates 220 and lateral bars 222, 224 define the central housing 202' which houses the probe or probes.

A pair of sliding skates 204 is hinged to each of said lower lateral bars 222, preferably at the end plates 220. Consequently, the sliding skates 204 oscillate around a rotation axis X coinciding with the longitudinal axis of the lower lateral bars 222. In other words, preferably, the sliding skates 204 oscillate on planes parallel to the end plates 220.

A practical example of such a skate with wheels and magnet, fitted so as to oscillate on a shaft, has been described in detail with reference to the oscillating support 150 relative to the embodiment of FIGS. 11 and 12.

The upper lateral bars 224 support at least one probe-holder bracket 230. In particular, said probe-holder bracket 230 comprises a guide element 232 attached or positionable along the upper lateral bars 224 and a sliding element 234 suitable to support the probe 300 and translate vertically in relation to said guide element 232. The probe-holder bracket 230 extends mainly in a transverse plane parallel to the end plates 220.

The guide element 232 has an upper portion 232' the lateral ends of which are crossed by the upper lateral bars 224. Preferably, the guide element 232 slides along the upper lateral bars 224 so as to be positionable in a desired intermediate position between the two end plates 220. In one embodiment, at least one of said lateral ends of the transverse portion 232' is vice-shaped provided with blocking screw 236 to permanently attach the probe holder bracket 230 in the desired position.

Two lateral guide portions 232" extend vertically downwards from the transverse portion 232' along which the sliding element 234 slides, for example by means of ball bearing skates.

Advantageously, said sliding element 234 is elastically connected to the guide element 232 by means of a compensation spring 238, which acts so as to press the sliding element 234 towards the resting surface. Such frame of the probe-holder bracket 230 thus guarantees a stable and constant contact of the probe 300 on the resting surface 2. Preferably, in addition, the loading of the compensation spring 238 may be modified by acting for example on an adjustment screw 240 supported by the transverse portion 232' of the guide element 232.

Figure 13:
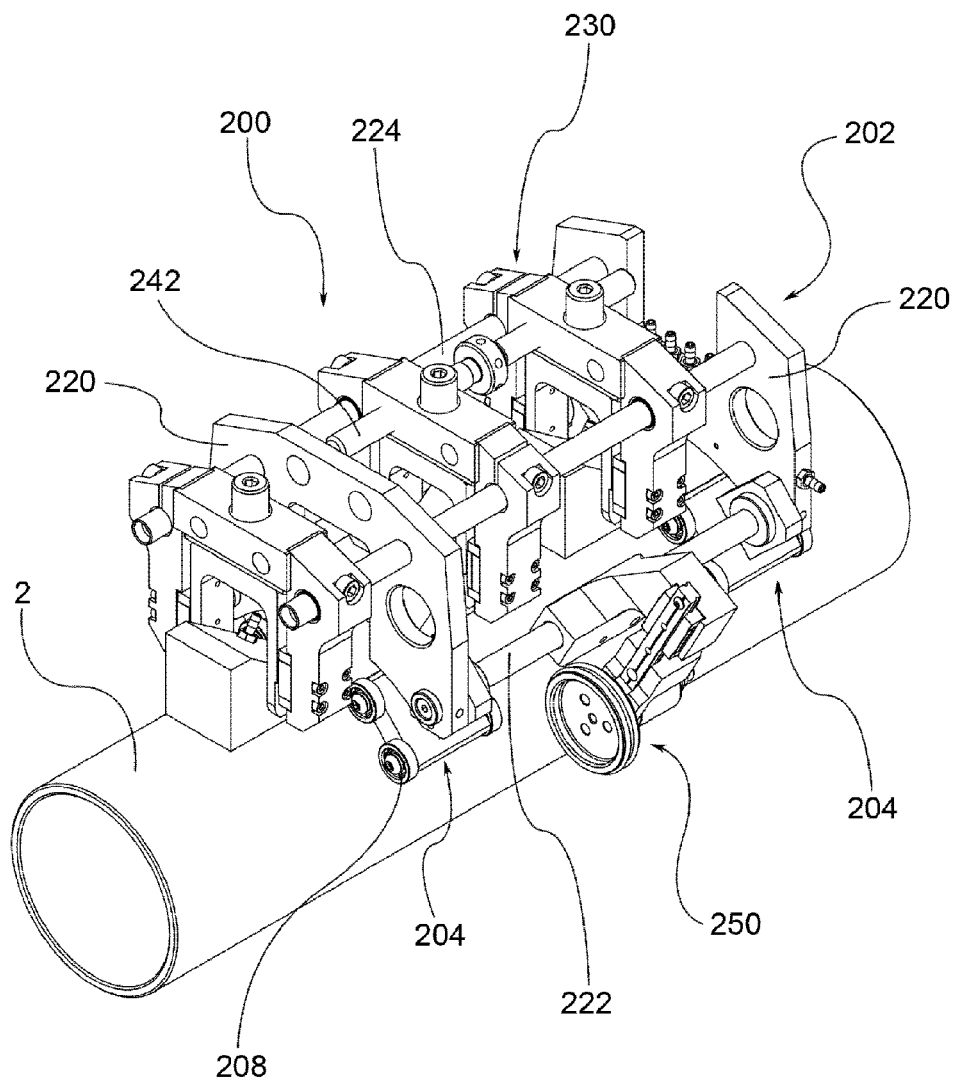
FIG. 13 is a perspective view of a probe-holder carriage in a further embodiment, fitted with probes and applied to a tube to be inspected.
Figure 14:
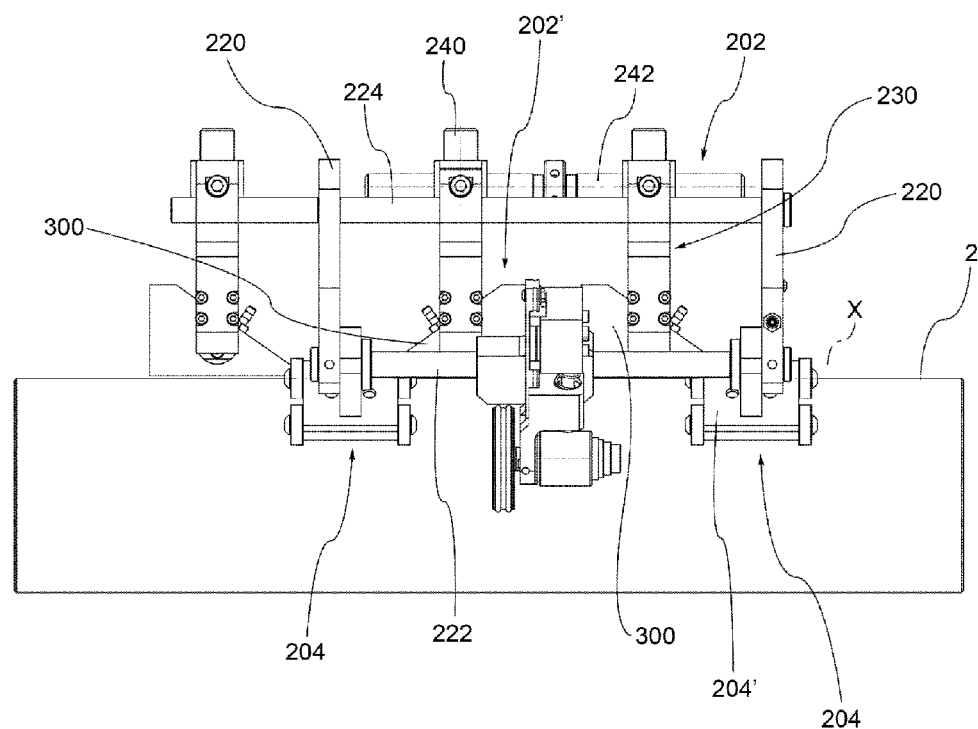
FIG. 14 is a side view of the probe-holder carriage.
Figure 15:
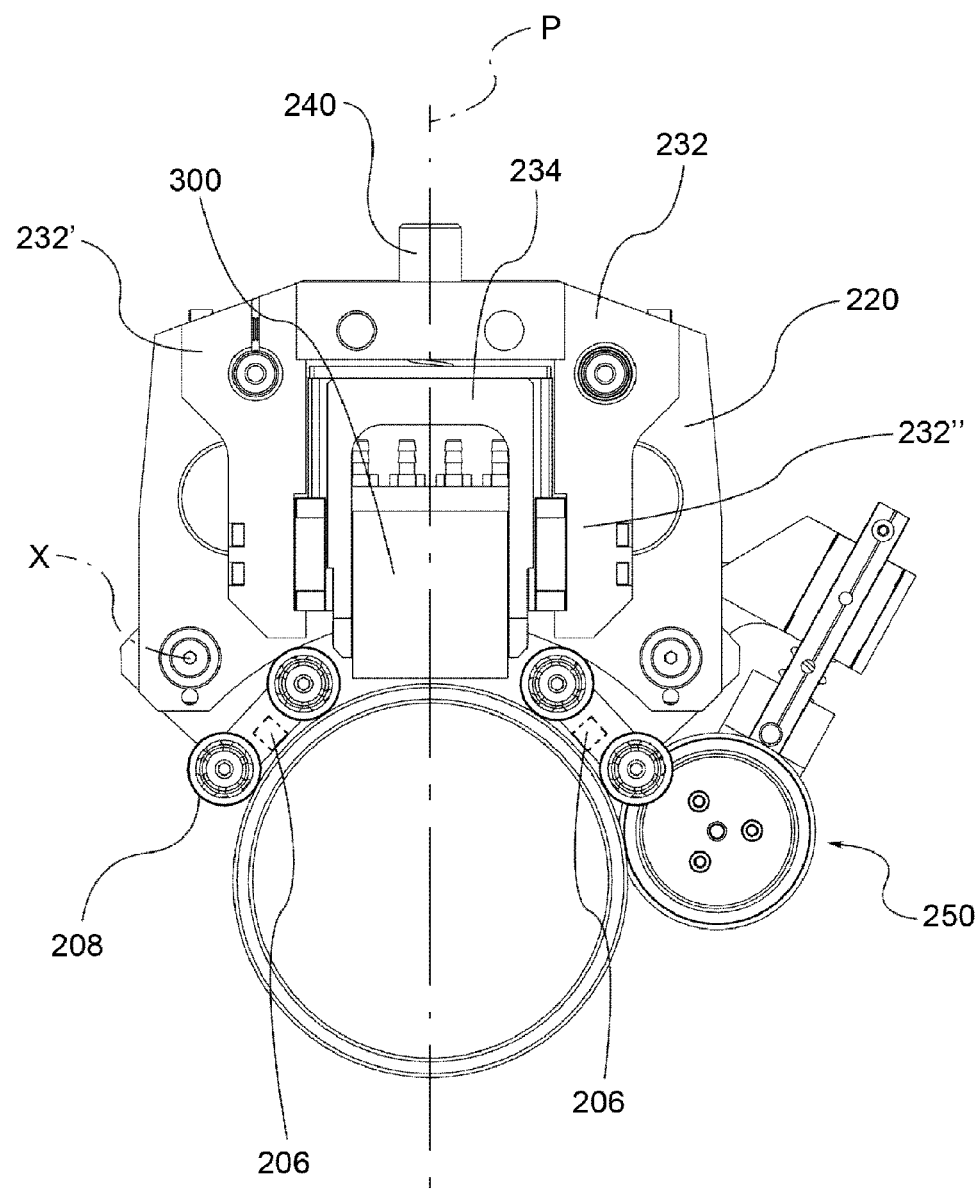
FIG. 15 is and end view of the carriage.

In the example shown in FIGS. 13-14, the probe-holder carriage 200 is fitted with two probe-holder brackets 230 between the end plates 220. The distance between the two probes may be finely adjusted by acting on an adjustment screw 242 which engaging threaded holes made in the guide element 232 of the brackets 230. In the embodiment illustrated, the upper lateral bars 224 may extend beyond one or both the end plates 220 to support a third or further probe-holder bracket 230.

In addition, in one embodiment, an encoder 250 or other detector sensor of the position of the carriage 200 in relation to the resting surface 2 may be attached to one of the lateral bars (lower 222 or upper 224).

Figure 19:
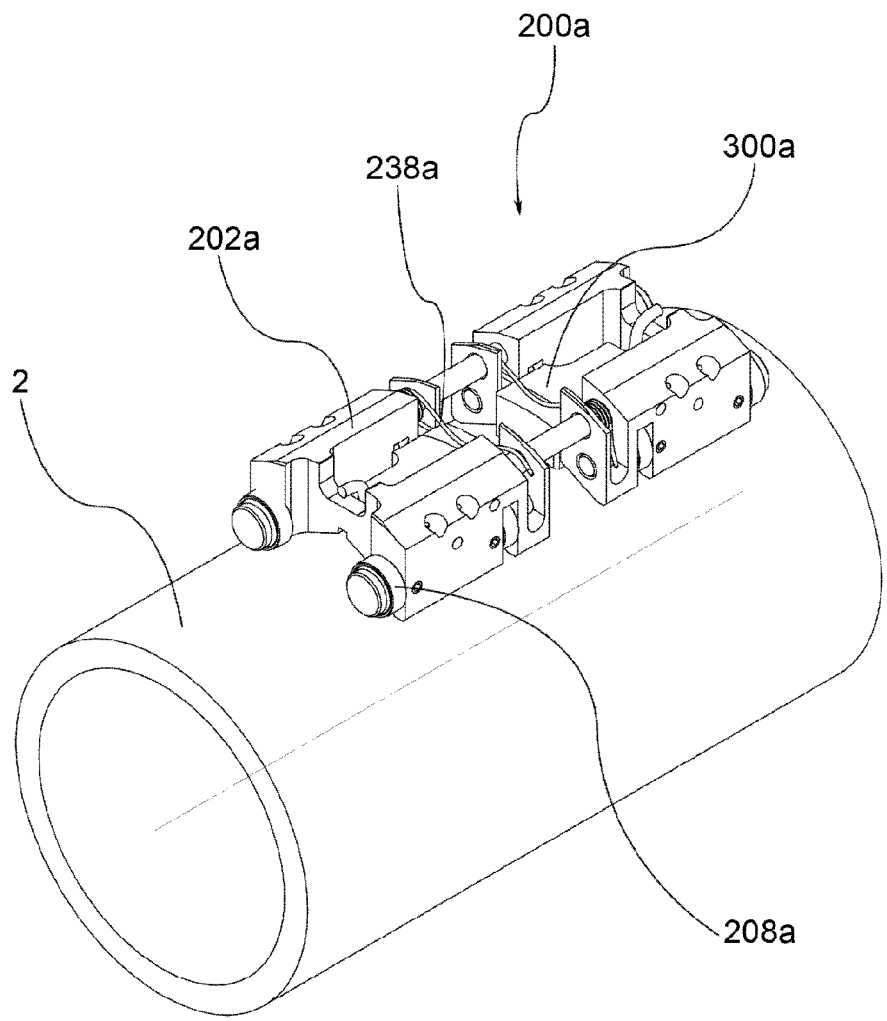
FIG. 19 is a perspective view of a probe-holder carriage in a still further embodiment, fitted with probes and applied to a tube to be inspected.
Figure 20:
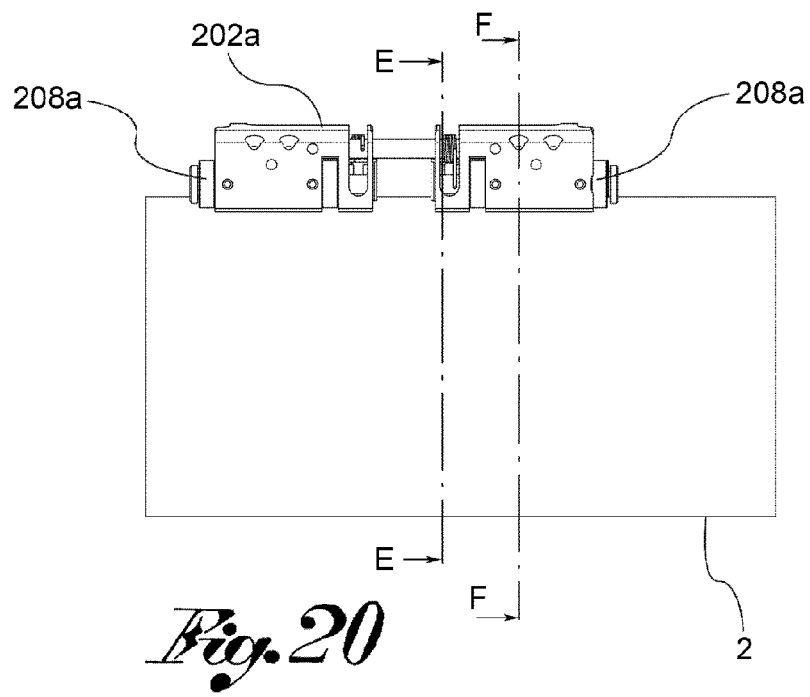
FIG. 20 is a side view of the probe-holder carriage.
Figures 20A, 20B:
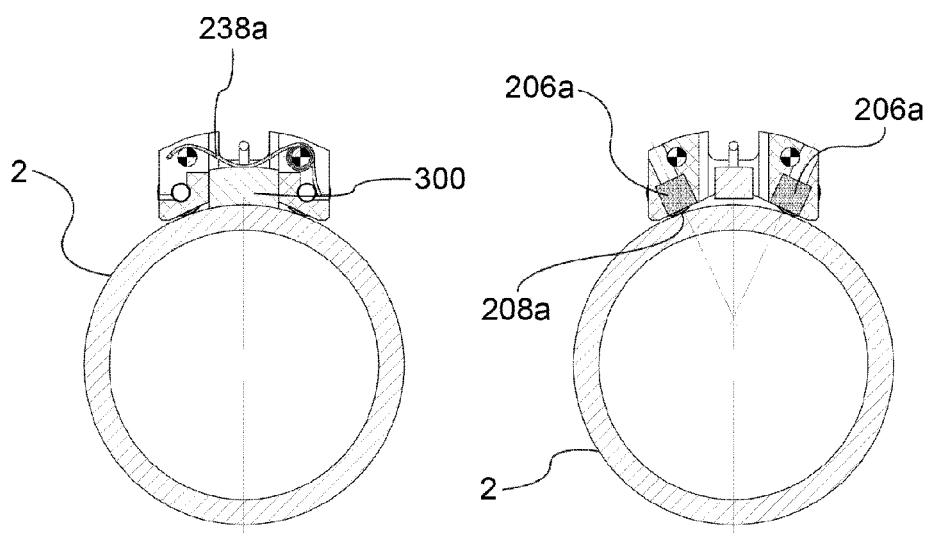
FIG. 20*a* is a cross section of the carriage along line E-E in FIG. 20.
FIG. 20*b* is a cross section of the carriage along line F-F in FIG. 20.

In a different embodiment of the probe-holder carriage illustrated in FIGS. 19-20, the sliding means comprise wheels or balls 208a fitted directly onto the probe-holder frame 202a.

In this embodiment, the permanent magnets 206a are supported directly by the probe-holder frame 202a.

In this embodiment, probe-holder frame 202a may have a concave or convex shape, as illustrated in the drawings, in such a way the carriage can slide also on convex or concave resting surfaces 2. In this embodiment, at least one probe 300a is fitted directly in a respective seat o recess made in the probe-holder frame 202a.

The probe 300a is pressed by a compensation spring into contact with the resting surface 2.

The probe-holder carriage described above may be easily moved along the resting surface thanks to the sliding means and is securely anchored to such surface thanks to the permanent magnets.

The frame of the probe-holder carriage makes it possible to position the probes in a central position in relation to such frame, ensuring constant and stable contact with the resting surface and thereby the maximum possible precision of detection. The presence of the tipping sliding skates enables the carriage to be used with the same precision of detection and safety, on curved surfaces too.

A person skilled in the art may, according to specific needs, modify, adapt or replace some elements with others of similar or identical function, without departing from the scope of the claims below. Each of the features described for a particular embodiment can be incorporated irrespective of the other forms of embodiment described.

What is claimed is:

1. A probe-holder carriage, comprising:
   a probe-holder frame,
   sliding means connected to said probe-holder frame and suitable for cooperating with a resting surface in a material with high magnetic permeability so as to permit a sliding of the carriage on said surface,
   at least one permanent magnet, suitable for interacting magnetically with said resting surface for an anchorage of the carriage to the resting surface, said permanent magnet being fitted so as to graze the resting surface with one of its poles, wherein:
   said probe-holder frame defines a central housing and comprises support means suitable to support at least one probe inside said central housing,
   said sliding means comprise sliding skates hinged to the probe-holder frame so as to be free to oscillate about an oscillation axis in relation to said frame to adapt to any curvature of the resting surface, wherein
   the at least one permanent magnet is supported by a respective sliding skate,
   the sliding skates are fitted with wheels suitable to permit a sliding of the carriage in one direction only,
   the at least one permanent magnet is kept in place at a predefined distance from the resting surface, and
   the rotation axis of the wheels is orthogonal to the oscillation axis of the sliding skates.

2. A carriage according to claim 1, wherein said sliding means comprise wheels or spheres fitted directly onto the probe-holder frame.

3. A carriage according to claim 1, wherein the probe-holder frame comprises two substantially vertical end plates connected by two lower lateral bars, two pairs of sliding skates being hinged to said lower lateral bars at said plates.

4. A carriage according to claim 3, wherein the sliding skates oscillate on planes parallel to the end plates.

5. A carriage according to claim 1, wherein the sliding skates are fitted with wheels suitable to permit a sliding of the carriage in one direction only.

6. A carriage according to claim 1, wherein the sliding skates are fitted with spheres suitable to permit a sliding of the carriage in any direction.

7. A carriage according to claim 3, wherein the end plates are connected by upper lateral bars which support at least one probe-holder bracket.

8. A carriage according to claim 7, wherein said probe-holder bracket comprises a guide element fixed to said upper lateral bars and a sliding element suitable to support the probe and to translate vertically in relation to said guide element.

9. A carriage according to claim 7, wherein said sliding element is elastically connected to the guide element by means of a compensation spring, acting so as to press the sliding element towards the resting surface.

10. A carriage according to claim 1, further comprising at least one probe fitted in the central housing and a compensation spring acting on said probe so as to press the probe into contact with the resting surface.

\* \* \* \* \*